United States Patent [19]

Bartels et al.

[11] Patent Number: 5,498,585
[45] Date of Patent: Mar. 12, 1996

[54] SULPHIDIZED CATALYST WHICH CONTAINS PLATINUM ON ACTIVATED CARBON

[75] Inventors: Karin Bartels, Hanau; Klaus Deller, Hainburg, both of Germany; Bertrand Despeyroux, Fourquex, France; Jochen Simon, Freigericht, Germany

[73] Assignee: Degussa Aktiengesellschaft, Frankfurt am Main, Germany

[21] Appl. No.: 259,677

[22] Filed: Jun. 13, 1994

[30] Foreign Application Priority Data

Jun. 14, 1993 [DE] Germany ............ 43 19 648.9
Apr. 26, 1994 [DE] Germany ............ 44 14 491.1

[51] Int. Cl.$^6$ .................................................. B01J 27/045
[52] U.S. Cl. .................................... 502/185; 502/222
[58] Field of Search ................................ 502/185, 222

[56] References Cited

U.S. PATENT DOCUMENTS 3,138,560  6/1964  Keith et al. ............... 252/447
4,889,704  12/1989  Fuchs et al. ............... 423/387

FOREIGN PATENT DOCUMENTS

| 0002651 | 8/1979 | European Pat. Off. . |
| 0467192 | 1/1992 | European Pat. Off. . |
| 0467174 | 1/1992 | European Pat. Off. . |
| 2150220 | 4/1974 | Germany . |
| 2303598 | 8/1976 | Germany . |
| 2736228 | 2/1978 | Germany . |
| 4218866 | 1/1994 | Germany . |
| 63-048761 | 4/1988 | Japan . |

*Primary Examiner*—E. Rollins Cross
*Assistant Examiner*—Timothy H. Meeks
*Attorney, Agent, or Firm*—Beveridge, DeGrandi, Weilacher & Young

[57] ABSTRACT

A sulphidized catalyst which contains platinum on activated carbon is described. The activity of the catalyst can be greatly improved, while retaining the same selectivity, when the platinum-containing impregnation solution contains an oxidizing agent.

12 Claims, No Drawings

SULPHIDIZED CATALYST WHICH CONTAINS PLATINUM ON ACTIVATED CARBON

BACKGROUND AND INTRODUCTION

The present invention relates to a sulphidized catalyst which contains platinum on activated carbon and a process for its preparation.

Sulphidized catalysts which contain noble metals have been prepared on a large scale and used for decades. A process for preparing this type of catalyst is described, for example, in DE-PS 21 50 220. A higher selectivity for the desired chemical reaction, generally with reduced catalyst activity, is produced by partial poisoning of the catalyst, by sulphidizing the catalyst which contains a noble metal with a compound which contains sulphur. Little is known about the sulphidizing mechanism itself, the nature of the sulphur bonded to the catalyst surface or the interactions between sulphur, noble metal and support.

For selective hydrogenation of halogenated nitroaromatic compounds (see, for example, prior printed German patent application P 42 18 866.0) and reductive alkylation (DE-OS 2736228), in particular, catalysts containing platinum as the noble metal and activated carbon as the support are preferred above all other catalyst systems.

The selectivity of these catalysts in these reactions is improved by partial poisoning by means of sulphidization.

Sulphur itself or other sulphur-containing compounds, such as $H_2S$, dimethyl sulphoxide, $(NH_4)_2S$, $Na_2S$, $Na_2SO_4$, are used as sulphidizing agents, wherein, e.g., the sulphur is released from the sulphur-containing compound by the action of a strong acid, such as $H_2SO_4$. In this case, concentrations of 0.1–10 moles of sulphur per mole of platinum, but preferably 0.1–2 moles of sulphur per mole of platinum, are used.

SUMMARY OF THE INVENTION

An object of the present invention is to improve a catalyst of this type, so as to obtain a catalyst which has a much better catalytic power than conventional catalysts following partial poisoning by sulphidizing with conventional sulphidizing agents. A further object is to produce improved catalysts by an improved process.

These and other objects of the invention are achieved by means of a sulphidized catalyst which contains platinum on activated carbon. The catalyst of the invention is obtainable by a process that involves mixing an aqueous solution of a platinum compound with an aqueous suspension of activated carbon. The resulting mixture is then heated to a temperature between 70° and 100° C. The platinum compound is precipitated with a base. After reducing the barely soluble platinum compound with a reducing agent at the same constant temperature, the product is filtered off and washed. The catalyst obtained in this way is then treated with a sulphidizing agent and washed again. An important feature of the invention is that the aqueous solution of platinum compound used in the initial reaction contains an oxidizing agent.

The platinum content of the final catalyst may be between 0.1 and 5 wt. % with respect to the activated carbon. Addition of an oxidizing agent to the aqueous solution of platinum compound before impregnating the powdered support of activated carbon leads, surprisingly, to a platinum-containing phase which greatly improves the catalytic performance after sulphidizing with conventional sulphidizing agents.

Also astonishing is the fact that the catalyst prepared by means of adding an oxidizing agent does not really exhibit an improved performance in catalytic reactions before sulphidizing.

DETAILED DESCRIPTION OF INVENTION

Suitable activated carbon supports which may be used are acid activated carbons and steam activated carbons with or without subsequent acid washing. Inorganic acids such as phosphoric acid or nitric acid are usually used for acid activation. Procedures for preparing activated carbon are well known in the art.

Activated carbon with a residual ash content of 1 to 5 wt. %, a pH higher than 4 and average particle diameters between 10 and 40 μm is produced, depending on the method of activation and the raw material used. The specific surface area of the activated carbon is very high and is normally between 500 and 1500 $m^2$/g. The total pore volume is generally greater than 0.5 ml/g.

To determine the pH of activated carbon, 1 g of activated carbon is suspended in 100 ml of water. The pH is measured at 25° C. after stirring for 5 minutes. Activated carbons with a pH higher than 5 are preferably used for the catalyst according to the invention.

Suitable oxidizing agents which may be used are inorganic percompounds, such as persulphates and perchlorates, sodium hypochlorite and alkyl hydroxyperoxides, but especially $H_2O_2$ at concentrations of 0.1–10 moles per mole of platinum, but preferably 0.5–5 moles per mole of platinum.

Suitable sulphidizing agents which may be used are all of the sulphur-containing agents known from the prior art.

On mixing the aqueous solution of platinum compound with the aqueous suspension of activated carbon, partial precipitation of a barely soluble platinum compound may take place and this is precipitated on the activated carbon. A base is added to the mixture of platinum-containing solution and activated carbon suspension for complete precipitation of the platinum as a barely soluble compound. Suitable bases are sodium carbonate, sodium hydroxide or potassium hydroxide. In general, inorganic alkaline compounds suitable for this purpose can be used.

A further object of the invention is to provide a process for preparing the sulphidized catalyst. This object is achieved by a process in which an aqueous solution of a platinum compound is mixed with an aqueous suspension of activated carbon, this mixture is heated to a temperature between 70° and 100° C., the platinum compound is precipitated with a base and the barely soluble platinum compound is reduced with a reducing agent at the same constant temperature, the catalyst obtained in this way is filtered off and washed, the catalyst is treated with a sulphidized agent and washed again. The process is characterized in that the aqueous solution of platinum compound contains an oxidizing agent. Completely deionized water (DI water) or distilled water is preferably used for washing the catalyst.

The aqueous suspension of activated carbon preferably has a concentration of 5 to 30 wt. %. Various water-soluble platinum compounds may be used, hexachlorplatinic acid hexahydrate having proved to be especially worthwhile.

The oxidizing agent, preferably hydrogen peroxide, is added to the platinum solution in an amount of 0.1–10 moles, preferably 0.5–5, mole of platinum.

The activated carbon suspension and platinum solution are mixed together and heated to 70° to 100° C., with stirring, before the platinum is precipitated onto the activated carbon, in the form of its barely soluble compounds, by the addition of a base, such as e.g. sodium carbonate or caustic soda solution, and then reduced at the same temperature, probably by the addition of a reducing agent such as hydrazine, sodium formate, sodium borohydride or formaldehyde, preferably formaldehyde.

The sequence of adding platinum solution and base to the activated carbon suspension is not important. Thus, the base may be added to the activated carbon suspension before introducing the platinum solution.

After filtering off and washing the Pt/C catalyst obtained in this way, the sulphidized agent, such as e.g. dimethyl sulphoxide or ammonium sulphide is added to the aqueous catalyst suspension, together with a strong acid such as sulphuric acid, at normal temperature.

The sulphidized catalyst should have a platinum content of 0.1–5, preferably 0.5–3.5 wt. %, and a sulphur content of 0.1–10, preferably 0.1–2 mole per mole of platinum.

As an alternative to the method of working described above, in which the solution containing oxidizing agent and platinum is added to the activated carbon suspension, the activated carbon may be contacted with by adding it to the solution containing oxidizing agent and platinum or the solution containing oxidizing agent and platinum may be sprayed onto the activated carbon.

To stabilize the platinum-containing solution, it may sometimes be advantageous to add an inorganic acid, such as hydrochloric acid, sulphuric acid or nitric acid, to the solution.

The invention is now explained by means of a few illustrative examples. Example 1 describes the preparation of the catalyst according to the invention and of comparison catalyst from the prior art. The activities of the non-sulphidized precursors of the catalyst were studied and compared with each other in a low-pressure tests. In example, 3, sulphidized catalyst according to the invention were tested for activity and selectivity in a high-pressure test and compared with the comparison catalysts.

Any suitable water soluble platinum compound which are already defined in the relevant prior art can be used for purposes of this invention as will be apparent to those skilled in the art.

EXAMPLE 1: Catalyst preparation

Activated carbon with the following physico-chemical characteristics was used as a support for all the catalysts:

| Material: | powdered activated carbon | |
|---|---|---|
| BET spec. surface area: | 1,500 m$^2$/g | (ASTM-D-3663) |
| Total pore volume: | 1.5 ml/g | (ASTM-D-4284) |
| Average particle size: | 22 μm | (ASTM-D-4464) |
| pH: | 10 | |
| Ash content: | <2% | |

A) Preparing the catalyst precursor (Pt+H$_2$O$_2$)/C (without sulphidizing)

To prepare a catalyst with 3% platinum load, 97 g of activated carbon (dry weight) were stirred into distilled water with a stirring speed of 300 rpm. 12 g of a 25% strength aqueous solution of hexachloroplatinic acid hexahydrate (corresponding to 3 g of Pt) and 3 ml of a 30% strength aqueous solution of H$_2$O$_2$, corresponding to 2 moles of H$_2$O$_2$ per mole of platinum, were added to this suspension.

Then the suspension was heated to 80° C. and sodium carbonate was added with continuous stirring, to precipitate barely soluble hydroxides. To reduce the precipitate, 1.8 ml of 37% strength formaldehyde solution was then added. The temperature of the suspension was also kept constant at 80° C. during reduction. After reduction, the catalyst was filtered off on a nutsch filter and washed with DI water.

B) Preparing the sulphidized catalyst according to the invention (Pt+H$_2$O$_2$+S)/C.

To prepare a catalyst with a 3% platinum load according to the invention, a catalyst was first prepared in accordance with part A and then sulphidized with dimethyl sulphoxide in accordance with example 1 in DE-PS 21 50 220. The total sulphur content of the sulphidized catalyst was about 0.4 moles of S per mole of Pt.

Catalyst with the same platinum load but with double or four-fold the sulphur content were prepared by appropriately increasing the amount of sulphidizing agent.

Catalysts with different platinum loads were made up using the same procedure as above with a simultaneous increase in the amounts of hexachloroplatinic acid, caustic soda solution and sulphidizing agent.

c) Preparing comparison catalysts: Pt/C

For comparison with the catalysts according to the invention, platinum-containing catalyst on activated carbon were prepared in the same away as in example 1, part A or B, but without the addition of H$_2$O$_2$.

EXAMPLE 2: Low-pressure test of catalyst precursors (without sulphidizing)

The activity of the catalyst precursors were tested in the hydrogenation of cinnamic acid under the following reaction conditions:

200 mg of catalyst were added to 10 g of cinnamic acid in 120 ml of ethanol and transferred to a 250 ml stirred reactor with a blow-stirrer, thermometer and hydrogen inlet.

The reactor was first carefully rinsed out with nitrogen at atmospheric pressure. Then a constant pressure of hydrogen of 10 mbar above atmospheric was set in the reactor at a reaction temperature of 25° C., and the hydrogen was dispersed uniformly in the solution via the blow-stirrer (2000 rpm).

The catalytic activity in the hydrogenation reaction of cinnamic acid to give dihydrocinnamic acid was used to measure the catalytic power and it is expressed in ml of hydrogen/g of catalyst/min. The time of reaction used for calculating this catalytic activity was the time of reaction between the 3rd and 8th minutes after the introduction of hydrogen.

Table 1 gives the test results for catalyst which were prepared as in example 1, part A or part C (without sulphidizing).

TABLE 1

| Example | Composition | Catalytic activity ml H$_2$/g catalyst/min |
|---|---|---|
| 1C | 3.0% Pt/C | 245* (220–280) |
| 1A | (3.0% PT + H$_2$O$_2$) /C | 240* (230–270) |
| 1C | 1.0% Pt/C | 95* (80–120) |
| 1A | (1.0% Pt + H$_2$O$_2$/C | 90* (70–110) |

*Average value after performing 10 experiments.

Table 1 shows that all the catalyst precursors have comparable activities.

EXAMPLE 3: High pressure test of the catalyst
(after sulphidizing)

The activity and selectivity of the catalyst according to the invention as in example 1B were compared with the activity and selectivity of comparison catalyst from the prior art, in accordance with example 1C, in the reductive hydrogenation of p-aminodiphenylamine (PADPA) with methylisobutyl ketone (MIBK).

For this purpose, 3.77 moles of PADPA were placed in 2 l autoclave together with 4.63 moles of MIBK and 1.38 g of a 3% Pt/C catalyst (corresponding to 0.2 wt. %, with reference to the amount of PADPA). The autoclave was sealed, rinsed first with nitrogen and then with hydrogen and a pressure of 50 bar of hydrogen was applied. The reaction mixture was heated to a temperature of 190° C. with stirring. Samples were withdrawn and analyzed after 60, 90 and 120 minutes of reaction time.

Table 2 gives the residual content of still unconverted PADPA in the analyzed samples and the hydrogenation time required to push the residual content of PADPA below 2 wt. %.

TABLE 2

| | High-pressure test Residual PADPA content % | | | Hydrogenation time [min.] at which residual PADPA content is <2% |
|---|---|---|---|---|
| | 60 min | 90 min | 120 min | |
| 1C (3.0 Pt + S)/C | 7.5 | 3.8 | 2.0 | 120 |
| 1C with double S | 11.3 | 5.9 | 2.8 | 135 |
| 1B (3.0 Pt + $H_2O_2$ + S)C | 3.6 | 1.8 | 1.0 | 86 |
| 1B with double S | 4.2 | 2.0 | 1.1 | 90 |
| 1B with four-fold S | 10.8 | 5.7 | 2.8 | 130 |

Table 2 shows that when using the catalyst according to the invention in accordance with example 1B, an improvement in activity of up to 35% above the prior art (example 1C) was achieved. The selectivity was not affected by the $H_2O_2$ treatment.

Further variations and modifications will be apparent to those skilled in the art from the foregoing and are intended to be encompassed by the claims appended hereto.

German priority document P 43 19648.9 is relied on and incorporated herein by reference.

We claim:

1. A sulphidized catalyst which contains platinum on activated carbon, having a platinum content of 0.1 to 5 wt % and a sulphur content of 0.1 to 2 moles per mole of platinum, produced by a method comprising contacting an aqueous solution of a platinum compound containing an oxidizing agent with activated carbon, heating the resulting product to a temperature between 0° and 100° C., precipitating the platinum compound with a base in the form of hydroxide and reducing the hydroxide with a reducing agent while keeping the temperature constant, filtering off and washing the catalyst obtained in this way, treating said catalyst with a sulphidizing agent and washing again, wherein the activated carbon has an average particle diameter of 10 to 40 μm, a specific surface area greater than 500 $m^2/g$, a total pore volume greater than 0.5 ml/g, a residual ash content of less than 5 wt. % and a pH higher than 5.

2. The catalyst according to claim 1 wherein the activated carbon is in the form of an aqueous suspension.

3. A process for preparing a sulphidized catalyst which contains platinum on activated carbon comprising contacting an aqueous solution of a platinum compound containing an oxidizing agent with activated carbon, heating to a temperature between 70° and 100° C., precipitating the platinum compound with a base in the form of hydroxide and reducing the hydroxide with a reducing agent while keeping the temperature constant, filtering off and washing the product obtained in this way, treating said product with a sulphidizing agent and washing again, wherein the activated carbon has an average particle diameter of 10 to 40 μm, a specific surface area of at least 500 $m^2/g$ a total pore volume greater than 0.5 ml/g, a residual ash content of less than 4 wt. % and a pH higher than 5.

4. The process according to claim 3 wherein an aqueous suspension of activated carbon is mixed with said aqueous solution.

5. The process according to claim 3 wherein the activated carbon is added to the solution containing oxidizing agent and platinum compound.

6. The process according to claim 3 wherein the solution containing oxidizing agent and platinum compound is sprayed onto the activated carbon.

7. A process according to claim 3 wherein hydrogen peroxide in an amount of 0.1 to 10 moles, preferably 0.5 to 5 moles per mole of platinum is used as an oxidizing agent.

8. The process according to claim 3 wherein said oxidizing agent is an inorganic per compound.

9. The process according to claim 8 wherein said per-compound is a member selected from the group consisting of persulfates, perchlorate, sodium hypochlorite, alkyl hydroxyperoxides and hydrogen-peroxide.

10. The process according to claim 3 wherein the activated carbon has a pH greater than 5.

11. The process according to claim 3 wherein the activated carbon has a residual ash content of 1 to 5 wt. %.

12. The process according to claim 3 wherein the activated carbon has a specific surface area of 500 to 1500 $m^2/g$.

* * * * *